United States Patent
Noack et al.

(10) Patent No.: US 9,465,006 B2
(45) Date of Patent: Oct. 11, 2016

(54) MODULATOR MONITORING DURING MEASURING ELECTROMOBILITY

(71) Applicant: Anton Paar GmbH, Graz (AT)

(72) Inventors: Harald Noack, Graz (AT); Christian Moitzi, Raaba (AT)

(73) Assignee: Anton Paar GmbH, Research & Development, Graz (AT)

( * ) Notice: Subject to any disclaimer, the term of this patent is extended or adjusted under 35 U.S.C. 154(b) by 499 days.

(21) Appl. No.: 14/091,892

(22) Filed: Nov. 27, 2013

(65) Prior Publication Data

US 2014/0144780 A1    May 29, 2014

(30) Foreign Application Priority Data

Nov. 27, 2012 (EP) ................................. 12194502

(51) Int. Cl.
G01N 27/447 (2006.01)
(52) U.S. Cl.
CPC .............. G01N 27/44721 (2013.01)
(58) Field of Classification Search
CPC .............................................. G01N 27/44721
See application file for complete search history.

(56) References Cited

U.S. PATENT DOCUMENTS

| 3,732,014 | A | * | 5/1973 | Uzgiris | ................ | G01J 3/4412 356/336 |
| 5,144,460 | A | * | 9/1992 | Barbanell | ................ | H04N 5/30 348/E5.085 |
| 7,295,311 | B2 | | 11/2007 | Nicoli et al. | | |
| 2002/0040851 | A1 | * | 4/2002 | Mc.Neil-Watson | ............ | G01N 27/44721 204/549 |
| 2003/0184838 | A1 | * | 10/2003 | Akiyama | ............. | G02F 1/0121 359/239 |
| 2011/0155650 | A1 | * | 6/2011 | McNeil-Watson | | G01N 27/44721 209/155 |
| 2011/0210002 | A1 | | 9/2011 | Hsieh et al. | | |
| 2014/0049771 | A1 | * | 2/2014 | Sadri | ................ | G01N 27/44791 356/51 |

FOREIGN PATENT DOCUMENTS

WO    WO2010041082 A2    4/2010

OTHER PUBLICATIONS

Tscharnuter, Walther W., Mobility Measurements by Phase Analysis, Applied Optics, Aug. 20, 2001, vol. 40, No. 24, Optical Society of America, pp. 3995-4003.

* cited by examiner

*Primary Examiner* — Tarifur Chowdhury
*Assistant Examiner* — Omar Nixon
(74) *Attorney, Agent, or Firm* — Robert A. Blaha; Smith Tempel Blaha LLC

(57) ABSTRACT

An apparatus for measuring information indicative of electromobility in a sample includes a light source for generating coherent light, a modulator that modulates the optical path length, particularly a reciprocatable modulator arranged for modulating a first part of the generated light, a sample cell for accommodating the measured sample for applying an electric field to the sample and for receiving a second part of the generated light for interaction with the sample in the electric field, a modulator monitor for monitoring the modulator by detecting interference between a first part of the light coming from the modulator and an unmodulated third part of the generated light, and a light detector arranged separately from the modulator monitor for detecting interference between a second part of light coming from the modulator and light received from the sample cell. The detected signal includes the information indicative of electromobility in the sample.

15 Claims, 2 Drawing Sheets

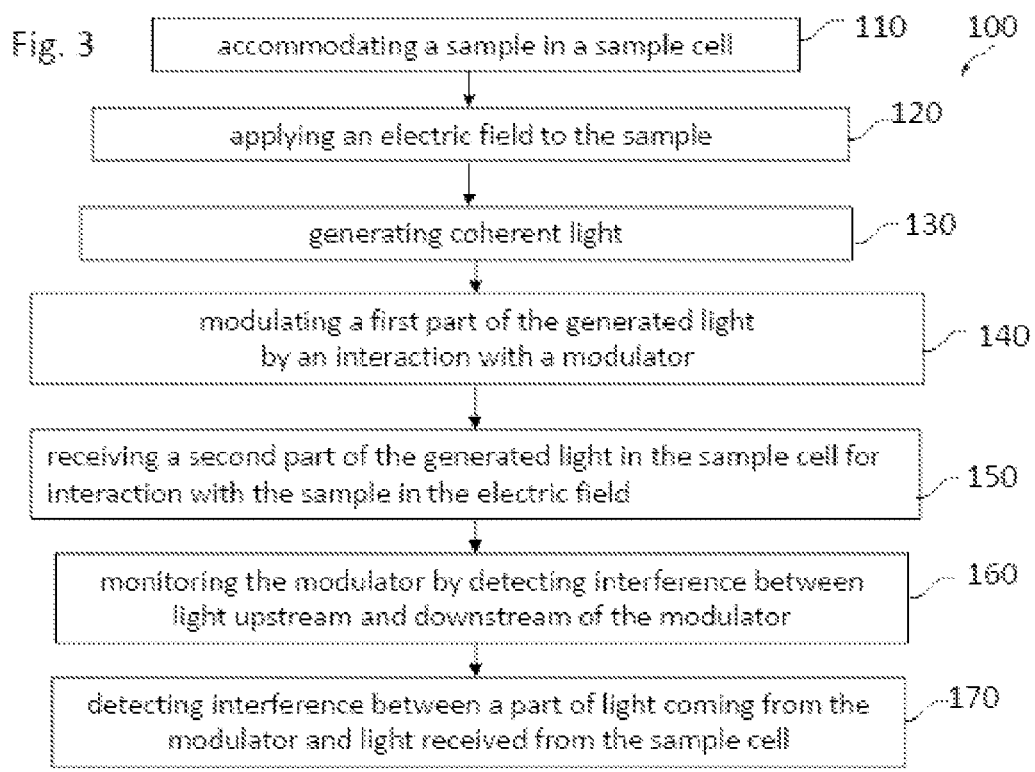

MODULATOR MONITORING DURING MEASURING ELECTROMOBILITY

CROSS REFERENCE TO RELATED APPLICATION

This application claims the benefit of the filing date of European Patent Application No. 12 194 502.6 filed Nov. 27, 2012, the disclosure of which is hereby incorporated herein by reference.

TECHNICAL FIELD

The invention relates to an apparatus for measuring information which is indicative of electromobility in a sample.

Furthermore, the invention relates to a method of measuring information which is indicative of electromobility in a sample.

BACKGROUND

The charge of particles in dispersion is of importance for their stability, rheological properties, coating behavior and other things. The zeta potential $\zeta$ is defined as potential at the surface of shear where the particle with a shell of electrostatically attracted counter ions moves through the bulk solution of a sample. The value of the zeta potential is not equal to the surface potential because of the bound ions. However, it is a relevant potential for describing the particle interaction in dispersion.

The electrophoretic mobility $\mu_e$, defined as the equilibrium velocity v the particle attains in an electric field E, can be related to the zeta potential according to the Henry equation by:

$$\mu_e = \frac{v}{E} = \frac{2\zeta \in f(\kappa\alpha)}{3\eta(T)} \quad (1)$$

where $\eta(T)$ is the viscosity as a function of the absolute temperature T, $\in$ is the dielectric constant of the dispersing medium, and $f(\kappa\alpha)$ is a function of the particle size $\alpha$ and the thickness of the double layer, the so-called Debye length $1/\kappa$.

The Smoluchowski approximation is valid for moderate ion concentrations and not too small particle size where $\kappa\alpha > 100$ and $f(\kappa\alpha)$ becomes 1.5.

For small particles in non-polar medium, where $\kappa\alpha < 1$, the Hückel approximation is valid. In this case $f(\kappa\alpha)$ becomes 1.

For intermediate values of $\kappa\alpha$, $f(\kappa\alpha)$ can only be determined numerically.

Laser Doppler Electrophoresis LDE (or Electrophoretic Light Scattering (ELS)) is an established technique for measuring the electrophoretic mobility of dispersed particles which is based on light scattering. In a suited arrangement of light source, detector, and electric field the scattered light experiences a frequency shift caused by the well-known Doppler-effect. In order to make this shift, which is small compared to the absolute light frequency, measureable the scattered light is mixed with a reference beam. The interference of the two contributions results in a beat with the Doppler-shift frequency.

Often a phase modulator is applied to the reference beam in order to create an additional frequency shift. This allows distinguishing between positive and negative frequency shifts corresponding to a positive and a negative sign of the zeta potential. Moreover, shifting the origin of the frequency spectrum to a non-zero value improves the stability and accuracy of the measurement of small, near-zero mobilities. The setup becomes less prone to thermal and mechanical changes.

The omnipresent random diffusive motion of the dispersed particles superimposes the collective electrophoretic motion. While the collective motion causes a Doppler shift, the diffusion causes a broadening of the spectral peak which in turn limits the accuracy of the measured Doppler frequency. Since the width of the spectral peak increases with $q^2$, whereas the Doppler shift scales only with q, it is beneficial to measure LDE at small scattering angles (small values of q). Here q is the magnitude of the scattering vector defined as:

$$q = \frac{4\pi n}{\lambda}\sin\left(\frac{\theta}{2}\right) \quad (2)$$

with n being the refractive index of the dispersing agent, $\lambda$ the wavelength of the incident beam, and $\theta$ the scattering angle.

At small scattering angles, however, the Doppler shift becomes small and long measurement times are needed in order to achieve sufficiently good statistical accuracy.

The cell walls carry charge, thus the application of an electric field causes the liquid adjacent to the wall to undergo electro-osmotic flow. However, in a closed system the flow along the walls must be compensated for by a reverse flow in the center of the cell. Dispersed particles will be subject to this flow superimposed on their electrophoretic mobility. Thus, in order to measure the electrophoretic velocity alone electro-osmotic effects have to be avoided. In addition electrode polarization, electrolysis and Joule heating may cause errors as well and have to be avoided too.

There are several approaches which proved to be effective.

First, there is a certain position in the sample cell where the electro-osmotic flow at the cell wall and the reverse flow in the center of the cell cancel. At this position, which is called the stationary layer, the particle velocity is unbiased by electroosmosis.

Second, the sign of the applied electric field can be reversed fast enough to avoid the formation of an electroosmotic flow, while the electrophoretic motion still reaches its equilibrium velocity. This means that the measured mobility is due to electrophoresis only and is not affected by electroosmosis. Fast reversal of the electric field also minimizes effects of electrode polarization and electrolysis. On the other hand, however, this effectively breaks the temporal averaging procedure of the signal into many short time batches.

In order to keep the energy input into the sample (the Joule heating) as small as possible the magnitude of the electric field has to be kept as low as possible. This in turn means that small Doppler shifts have to be measured.

Phase Analysis Light Scattering (PALS) is a modification of Laser Doppler Electrophoresis which makes it possible determining small frequency shifts by measuring a series of short intervals.

Rather than analyzing the beat frequency (for instance by Fourier transformation), PALS is looking at the change of phase with time. Obviously, this rate is equivalent with the frequency. However, recasting the problem in this way makes it possible to evaluate signals where only a fraction of a Doppler cycle is available and greatly increases the sensitivity for small velocities of the particles.

PALS makes it possible to make use of the short measurement intervals needed to avoid electroosmosis, electrode polarization, and electrolysis by fast reversal of the electric field. The statistical accuracy is reached by averaging many such short intervals. Nevertheless even when PALS is used, it is still beneficial to keep the time intervals which are measured in a phase-locked way as long as possible.

In PALS the rate of phase change of the measured interference between scattered beam from the sample and the modulated reference beam is analyzed. This rate is compared with a mathematically generated sine wave predetermined by the modulator frequency.

Any non-linearity of the modulator and any change in the characteristics of the modulator (for instance because of a change in temperature, change in the frequency or aging) will cause a situation where the mathematically generated frequency does not reflect the real conditions any more. Ideally, the generated wave corresponds to the beat frequency when the particles in the sample are not moving. The electrophoretic mobility and in turn the zeta potential is determined from the frequency difference (difference in rate of phase change) due to the Doppler shift. Thus, any error in the mathematically generated frequency translates into an error of the zeta potential.

For Laser Doppler Electrophoresis and also for PALS it is beneficial to produce the interference between scattered beam from the sample and the modulated reference beam for a long period of time in a phase-locked way. Thus, the use of a modulator with a large phase-range is increasing the stability and accuracy of the measurement.

Modulators with a large total phase-range are usually not linear. This means for instance for a piezo or voice-coil driven modulator that a linearly increasing voltage or current does not cause a linear motion of the modulator. Such a non-linearity of the modulator is resulting in a temporal change of the beat frequency during the move. In addition the characteristics of such a modulator also vary with temperature, frequency and age. This behavior is not compatible with the standard PALS method because no simple function can be generated which is correctly describing the characteristics of the modulator.

Conventional systems of determination of the electrophoretic mobility are disclosed in US 2011/0210002 A1, WO 2010/041082 A2, U.S. Pat. No. 7,295,311 B2, J. F. Miller, K. Schätzel, and B. Vincent, "The determination of very small electrophoretic mobilities in polar and nonpolar colloidal dispersions using phase analysis light scattering", Journal of Colloid and Interface Science, 1991, 143(2): p. 532-554, and F. McNeil-Watson, W. Tscharnuter, and J. Miller, "A new instrument for the measurement of very small electrophoretic mobilities using phase analysis light scattering (PALS)", Colloids and Surfaces A: Physicochemical and Engineering Aspects, 1998, 140(1-3): p. 53-57.

In conventional apparatuses, a mathematically generated wave is used for the demodulation of the Laser Doppler Electrophoresis signal. Modulator non-linearity causes an error in the determination of the electrophoretic mobility. Temporal changes of the modulator characteristics, for instance with temperature, frequency or age, cause an error in the measured electrophoretic mobility.

SUMMARY

There may be a need for an efficient measurement of electrophoretic mobility of particles in a sample.

According to an exemplary embodiment of the invention, an apparatus for measuring information which is indicative of electromobility in a sample (particularly a dispersion, more particularly particles under observation in a fluidic, for instance liquid, matrix) is provided, wherein the apparatus comprises a light source configured for generating coherent light (i.e. electromagnetic radiation of an appropriate frequency or frequency range, for instance visible light in a range between 400 nm to 800 nm, ultraviolet light or infrared light), a modulator (particularly a modulator that modulates the optical path length) arranged for modulating a first part of the generated light, a sample cell for accommodating the measured sample, configured for applying an electric field to the sample, and arranged for receiving a second part of the generated light for interaction with the sample in the electric field, a modulation monitor configured for monitoring the modulator by detecting interference between a first part of the light coming from the modulator and an unmodulated (i.e. not modulated due to an interaction with the modulator) third part of the generated light, and a light detector arranged separately from the modulator monitor and being configured for detecting interference between a second part of light coming from the modulator and light received from the sample cell, wherein the detected signal includes the information which is indicative of electromobility in the sample (particularly the value of the electromobility of particles in the sample is determinable or determined from the signal detected by the light detector).

According to another exemplary embodiment of the invention, a method of measuring information which is indicative of electromobility in a sample accommodated in a sample cell to which an electric field is applied is provided, wherein the method comprises generating coherent light, modulating a first part of the generated light by an interaction with a modulator, receiving a second part of the generated light in the sample cell for interaction with the sample in the electric field, monitoring the modulator by detecting interference between a first part of the light coming from the modulator and an unmodulated third part of the generated light, and—separately from the monitoring—detecting interference between a first part of the light coming from the modulator and an unmodulated third part of the generated light, wherein the detected signal includes the information which is indicative of electromobility in the sample.

According to an exemplary embodiment of the invention, a failure-robust and artifact-free measurement system is provided which is particularly appropriate for Phase Analysis Light Scattering (PALS). In such an embodiment, a coherent light beam is directed partially through a sample cell to which an electric field is applied. Depending on the electromobility of the particles of the sample in the sample cell, a characteristic Doppler shift will be applied to the light which can be detected by an interference between this light downstream of the sample cell with a reference beam of light. However, before being brought into interference with the light beam having interacted with the sample, the reference beam is made subject to an interaction with a, for instance reciprocating, modulator that modulates the optical path length which results in another Doppler shift of the reference beam. Depending on the values of the two Doppler shifts applied to the reference beam by a certain actual optical path length alternation rate of the modulator on the one hand and applied to the beam propagating through the sample by the movement of the particles of the sample in the electric field on the other hand, a signal with a certain characteristic can be detected by the light detector in view of the resulting (constructive or destructive) interference. However, it may happen that the modulator behaves in a non-ideal manner, for instance it may show a non-linear behavior in view of intrinsic effects within the modulator and/or due to temperature or pressure effects or aging effects. In order to monitor such a non-ideal behavior resulting in a measurement artifact, a part of the reference beam having passed the modulator is made to interfere with another partial beam of original light coming directly from the light source. In the absence of the disturbing artifacts, the correspondingly measured signal of the modulation monitor indicates an ideal time-optical path length alteration rate relationship of the modulator. However, in case of non-ideal behavior, the signal detected by the modulation monitor will be influenced and will deviate from a target shape. Thus, the signal measured by the modulation monitor may be used as an indication whether there is a risk of modulator-related artifacts in the actual measurement signal detected by the light detector. In an embodiment, it is possible to use portions of the reference beam before and after the modulator, detect it for instance with a separate photodiode (no array detector is needed), and the signal may be used as modulator monitor.

More particularly, a first fraction of the reference beam is split off before (or upstream) the modulator and a second one after (or downstream) the modulator, and both are brought to interference by an appropriate optics. The arising beat may be detected simultaneously to the actual detection signal (for instance an LDE signal) and allows to monitor the characteristics of the modulator. Instead of a mathematically generated wave this monitor signal may be used for the demodulation of the detection signal as measured by the light detector in a for instance continuously monitored PALS method.

Compared to the intensity which is scattered from the particles, the light intensity in the monitor interferometer is much larger and can be measured with a smaller signal to noise ratio. Furthermore, the beat frequency of the monitor interferometer is only generated by the optical path length alternation of the modulator and no broadening of the line width by diffusive particle motion is added. Thus, the rate of phase change (as a function of time) which corresponds to zero motion of the particles can be measured at a high precision simultaneously to the actual detection signal (for instance an LDE signal). This in turn allows for a correct determination of the rate of phase change caused by the particle motion and the zeta potential.

Exemplary embodiments of the invention have the advantage that any modulator non-linearity may be compensated. Changes in the characteristics of the modulator, for instance because of changes in temperature or frequency or because of aging, can be partially or fully compensated. The monitor interferometer may measure the modulator characteristics for instance continuously and parallel to the sample measurement. The monitor interferometer is totally independent of sample properties. The monitor is always working at high intensity and failure-robust conditions. The monitor signal does not suffer from broadening of the spectral line width because of diffusive particle motion. It does not suffer from (forward) scattering of the particles in the sample. A ratiometric architecture according to an embodiment of the invention may compensate every drift caused by the modulator.

DESCRIPTION OF EXEMPLARY EMBODIMENTS

In the following, further exemplary embodiments of the apparatus and the method will be explained.

In an embodiment, the apparatus is configured as a Phase Analysis Light Scattering (PALS) apparatus for measuring electromobility by Phase Analysis Light Scattering. In other words, measurement of the electromobility of particles in the (particularly fluidic, more particularly liquid and/or gaseous) sample is performed using a PALS system, as described in the section describing the background of the invention (to which section explicit reference is made in the context of the disclosure of embodiments of the present invention).

In an embodiment, the apparatus is configured as a Laser Doppler Electrophoresis apparatus for measuring electromobility by Laser Doppler Electrophoresis. In other words, measurement of the electromobility of particles in the (particularly fluidic, more particularly liquid and/or gaseous) sample is performed using an LDE (or Electrophoretic Light Scattering ELS) system, as described in the section describing the background of the invention (to which section explicit reference is made in the context of the disclosure of embodiments of the present invention).

In an embodiment, the modulator (for instance at least a light-reflecting surface of the modulator at which the corresponding light beam is reflected) is configured for moving to thereby phase-modulate the first part of the generated light interacting with the moving modulator. Since the modulator moves, it will influence the part of the original light beam being reflected at the modulator in accordance with the Doppler effect. This will have an impact on the phase, and/or the frequency, of the reflected light.

In an embodiment, the modulator is configured for reciprocating (i.e. alternatingly moving in a forward and a backward direction in relation to the beam propagation) for modulating the first part of the generated light. Depending on the present motion velocity and direction of the modulator, the influence on the part of the original light beam will also change over time which results in a modulation of this light beam. The reciprocation may be a ramp-like reciprocation. The reciprocation may have a predefined periodicity.

In an embodiment, the modulator comprises a retroreflector arrangement of two reflection mirrors configured for double-reflecting the first part of the generated light. Such a double reflector may allow to change the propagation direction of the light by 180°, wherein the light beam will be reflected twice and the phase modulation range is doubled.

In an embodiment, the modulator comprises a piezo drive configured for moving upon applying an electric drive signal to a piezoelectric body of the piezo drive. A piezo drive can be considered as a piezoelectric body to which a voltage is applied so that the body moves in dependence of the applied electric field or signal. Such a piezo modulator may allow to manufacture the apparatus in a compact way, however a piezo drive is prone to non-ideal behavior. By adding a modulator monitor to such a piezo modulator allows to increase the accuracy of the measurement while maintaining the well-established and compact concept of a piezo drive.

The used piezo modulator may be moved by applying an electric drive signal (a voltage or current signal), such as a periodic ramp-like drive signal. This drive signal may trigger the piezo modulator to perform an elongation (i.e. a difference in dimension of the piezo between the minimum of the drive signal and the maximum of the drive signal) in a range between 2 µm and 1000 µm, particularly in a range between 20 µm and 100 µm. Advantageously, a piezo stack may be used in order to obtain sufficiently large elongations. When using visible light (with a wavelength between 400 nm and 800 nm) for the beams propagating along the apparatus, the elongation of the piezo modulator may be many times of the light wavelength resulting in a sufficiently large number of light-dark transitions in the detection signal and therefore a proper measurement accuracy. The elongation should not be larger than the coherence length of the light source. If the elongation becomes however too large, problems with linearity of the modulator may occur. Such problems may however be overcome by taking into account the signal of the modulator monitor (for instance for correcting the detection signal and/or the drive signal). The piezo may be moved with a drive frequency in a range between for instance 1 Hz and 50 Hz, for instance 5 Hz.

The modulator may or may not be movable. Particularly, the modulator is a reciprocatible, optical path length modulator in one embodiment. In another embodiment, the modulator is of the type that modulates the refractive index which results in a modulation of the optical path length.

In an embodiment, the modulator monitor and the light detector are physically and spatially separate bodies. In other words, the modulator monitor and the light detector may be separate members being movable and arrangable independently from one another at desired different positions and orientations along the beam paths of the system. They may also function independently. Thus, the modulator monitor and the light detector may also be operated independently from one another so that each of them may be configured, located and operated without and regardless of the other one. This provides a large freedom in designing the system and adapting it to the requirements of measurement signal detection on the one hand and modulator monitoring on the other hand.

In an embodiment, the modulation monitor is configured so that the unmodulated third part of the generated light (i.e. light which has not interacted with the modulator so that the modulator has not applied a phase or frequency shift to this third part) propagates onto the modulation modulator without prior interaction with the sample in the sample cell. In other words, the unmodulated third part is not influenced at all by any properties of the sample and is not influenced at all by any properties of the sample cell (such as a present electric field and related properties) so that it is a pure fingerprint of the light emitted by the light source. Apart from optional optical elements such as reflectors or beam splitters which may be arranged between the light source and the modulation monitor, the emitted light is directed directly onto the modulation monitor.

By detecting an interference between light having the original properties of the light source and such light after interaction with the modulator as modulation monitoring signal, it is not necessary to use an array of photodiodes for evaluating the modulation monitoring signal. The use of a single photodiode may be sufficient, because the signal's intensity alone allows to derive the modulator characteristic, particularly to identify artifacts of the modulator. More particularly, the signal of such a photodiode may be directly used for correcting or compensating for non-idealities of the modulator and/or for processing the detection signal detected by the light detector.

In an embodiment, the apparatus comprises a determining unit (such as a processor) configured for determining information indicative of the electromobility or electrophoretic mobility of the sample (for instance for quantitatively determining a value of the electromobility) based on the signal detected by the light detector and based on modulator information (such as the modulation monitoring signal itself) detected by the modulation monitor. According to such an embodiment, the actual measurement signal measured by the light detector (which may also be a single photodiode) may be corrected in order to at least partially compensate for the artifacts of the modulator as monitored by the modulator monitor. Therefore, the detection signal at the end of the propagation path of the light beams may be corrected by taking into account a non-ideal behavior of the modulator, as indicated by the signal sensed by the modulator monitor.

In an embodiment, the determining unit is configured for determining the information by demodulating the signal detected by the light detector using the modulator information (such as the modulation monitoring signal itself). Particularly, the demodulation may be performed using directly the signal measured by the modulator monitor which allows for a fast and precise compensation of modulator artifacts. The detection signal as measured by the light detector (for instance an LDE signal) is caused by the modulator motion and the motion of the particles (superposition of collective electrophoretic motion and the random diffusive motion). Demodulation of the detection signal with the measured monitor signal guarantees that the motion of the particles is determined correctly independent of modulator non-linearity and temporal changes of the modulator characteristics.

In an embodiment, the modulator information is indicative of a deviation of an actual modulator behavior from a target modulator behavior. Particularly, the modulator information is indicative of a modulator artifact, a non-linear behavior of the modulator, an impact of environmental conditions such as temperature or pressure on the behavior of the modulator and/or aging effects changing behavior of the modulator over time. However, any other kinds of undesired behavior of the modulator or deviation from a target behavior can also be at least partly compensated according to exemplary embodiments of the invention because the signal as detected by the modulation monitor does not rely on any physical model for the deviation, but merely measures this deviation on a phenomenological level.

In an embodiment, the determining unit is configured for manipulating the signal detected by the light detector to thereby at least partially compensate for a deviation between a target beat frequency and an actual beat frequency of the modulator. By a merely mathematical operation, the influence of the non-ideal behavior of the modulator on the detection signal may be eliminated partially or entirely by the determining unit.

In an embodiment, the apparatus comprises at least one optical element, particularly a reflector mirror, arranged in a beam path between the sample cell and the light detector and being configured for directing only a part of the light having interacted with the sample in the electric field towards the light detector which part has been scattering into a predefined angular range. Particularly, a center of the predefined angular range is slanted relative to a direction of the second part of the generated light impinging on the sample cell or leaving the sample cell without scattering. According to this embodiment, the measurement of the electromobility is performed under a non-zero scattering angle. For instance, scattering angles in a range between 5° and 50°, particularly between 10° and 20° may be considered.

In an embodiment, the apparatus comprises a beam splitter arranged for splitting a light beam coming from the light source into the first part of the generated light and into the third part of the generated light. A beam combiner may be arranged for combining the first part of the light coming from the modulator and the third part of the generated light and for directing the combined light to the modulator monitor. However, it is a matter of choice whether the part of the light being reflected or transmitted by the beam splitter is used for combination with the other component. It is only important that the signal detected by the modulator monitor results from an interaction of light before and after manipulation by the modulator.

In an embodiment, the apparatus comprises a reference beam intensity adjustment unit, particularly a variable attenuator, arranged in a beam path downstream of the modulator and upstream of the light detector and being configured for adjusting intensity of the second part of light coming from the modulator. By such an adjustable reference beam intensity adjustment unit, it is possible to manipulate the reference beam to an intensity value which is appropriate for interference with the beam downstream of the sample cell.

In an embodiment, the apparatus comprises a sample beam intensity adjustment unit, particularly a variable attenuator, arranged downstream of the light source and upstream of the sample cell and being configured for adjusting intensity of the second part of the generated light. Therefore, the original light may be adjusted to a desired intensity value before interaction with the sample cell.

In an embodiment, a beam path from the light source via the modulator to the light detector and a beam path from the light source to the modulator monitor are both entirely apart from the sample cell and free of an interaction with the sample. By taking this measure, it may be ensured that the modulator monitor detects a signal which is not influenced at all by any properties of the sample. In contrast to this, this signal is purely and precisely indicative of artifacts originating from non-ideal modulator behavior only.

In an embodiment, the modulation monitor is configured as a single sensor element, such as a single photodiode. In an embodiment, the light detector is configured as a single sensor element, such as a single photodiode. Both these embodiments allow for constructing the apparatus very compact and allow for a very simple and fast processing of the detected signals for determining the modulator performance and the value of electromobility.

Advantageously, the light detector may be configured as a single photon counter.

In an embodiment, a Doppler shift (for instance 0 Hz to 100 Hz) applied to the light by the electric field moving sample particles in the sample cell shall, to prevent aliasing, be smaller, for instance 10 times smaller, than the Doppler shift (for instance 100 Hz to 5000 Hz) applied to the light by the modulator. Then, the measurement of the beat is very accurate.

Particularly, the entire apparatus may be free of array detectors. Individual photodiodes or another individual sensor pixel, rendering the evaluation of the signal easy and the apparatus compact, are sufficient for detecting signals on the side of the modulation monitor and on the side of the light detector.

In an embodiment, the modulation monitor is configured for regulating a drive signal, which is to be applied to the modulator for moving the modulator in response to the applied drive signal, based on a signal detected by the modulator monitor resulting from the interference between the first part of the light coming from the modulator and the unmodulated third part of the generated light. Therefore, the modulator monitor may be connected, via a feedback line or the like, to the drive unit for mechanically driving or moving the modulator. By modifying or adapting the drive signal based on a detected artifact of the modulator behavior allows for a correction of the drive signal essentially in real-time. Therefore, based on the phenomenological detection of the real behavior of the modulator, its drive signal may be adjusted so as to approach a target behavior of the modulator. This embodiment may be implemented additionally or alternatively to the use of the signal of the modulator monitor for the purpose of actively correcting the detection signal. For example, the target drive signal may be ramp-shaped. However, upon determining a non-linear actual behavior of the modulator upon applying the drive signal, the drive signal may be regulated to be different from the ramp-shape so that the manipulated drive signal produces a linear behavior of the modulator.

In an embodiment, the modulation monitor is configured for regulating the drive signal for linearizing the motion of the modulator. Again referring to the previously described embodiment, the goal of the feedback signal or regulation signal sent from the modulator monitor to the drive (such as a voltage source) of the modulator is to provide a linear behavior of the modulator.

In an embodiment, the modulator monitor is configured for continuously monitoring the modulator by detecting modulator information over a continuous time interval during at least a part of the entire duration of a Phase Analysis Light Scattering measurement. In such an embodiment, monitoring may be performed over an uninterrupted time interval, for instance over the duration of the whole measurement. Thus, modulator-related artifacts may be prevented over the whole measurement or at least a continuous part thereof. In such an embodiment, no mathematically generated wave needs to be used but the measured signal (for instance an LDE signal) is demodulated with the monitor signal which is measured continuously and parallel to the (for instance LDE) measurement.

In another embodiment, the modulator monitor is configured for discontinuously (or intermittently) monitoring the modulator by detecting modulator information only at a number of defined points of time spaced and separated relative to one another over the duration of a Phase Analysis Light Scattering measurement. Such an embodiment is very simple in terms of signal evaluation, since monitoring of the modulator performance is only done on certain occasions (such as a suspicion or receipt of a user command) or after the expiry of a certain time interval.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

FIG. 3 illustrates a PALS method according to an exemplary embodiment of the invention.

DETAILED DESCRIPTION

Figure 1:
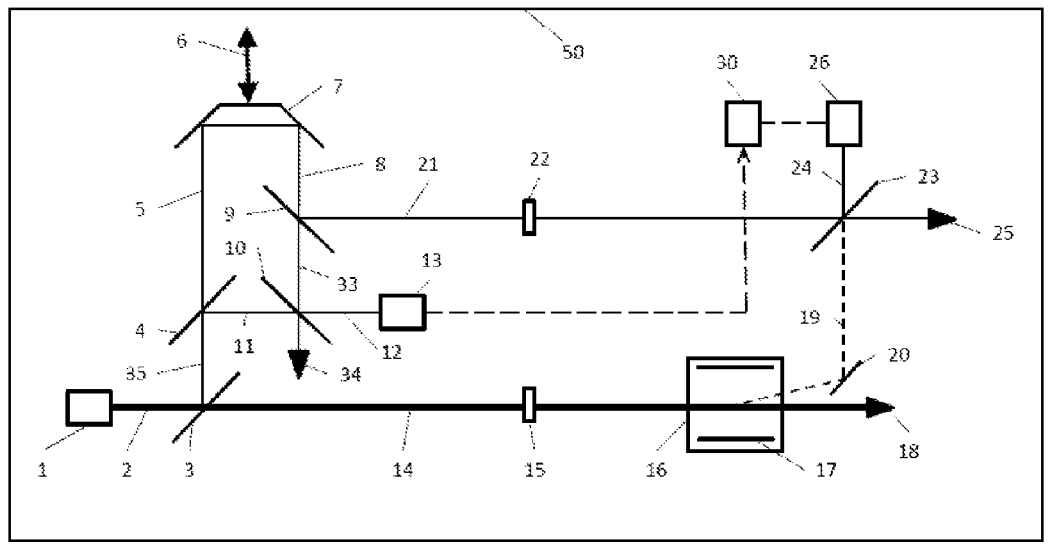
FIG. 1 illustrates a PALS apparatus according to an exemplary embodiment of the invention.

The illustrations in the drawings are schematical. In different drawings, similar or identical elements are provided with the same reference signs.

According to an exemplary embodiment of the invention, a modified PALS method and apparatus are provided by which an electric charging of particles under dispersion can be determined. By an electric field, these particles are set in motion. The velocity of this motion (electrophoretic mobility) can be detected by an interferometric measure method. However, piezo elements as an example for a phase modulator (but the similar statement also holds for other phase modulators) are in many cases not operating perfectly, particularly in case of large phase ranges. However, for a precise measurement, a long-term measurement with a phase coupled modulation is desired. Thus, phase modulators with a great stroke or phase range are also desired. In order to overcome this conventional dilemma, an exemplary embodiment of the invention implements a monitor interferometer in parallel to a measurement interferometer. The former measures the beads of modulated and non-modulated beams (both beams are not coming in interaction with the sample). This bead is also only dependent on the motion of the modulator. It is measured by a separate photodiode, wherein this signal may be used for a demodulation of the measurement signal. By taking this measure, it can be guaranteed that the part of the frequency shift which results from the particles is correctly determined. Non-linearities and instabilities of the modulator can be at least partially compensated.

With such a system, a non-linearity of the modulator can be equilibrated. Changes in the modulator characteristic can be equilibrated as well. The measurement of the modulator characteristic may be performed parallel to the measurement and for instance during the entire measurement of the detection signal. Hence, a ratiometric measurement method may be applied in which the measurement of the monitor signal is completely independent of the properties of the sample and therefore provides highly reliable results. The monitor signal is therefore also not influenced by the motion of the particles. The monitor signal is also not influenced by stray light or scattered light (particularly forward scattering) of the sample.

The modulator channel cannot only be used for correcting a non-ideal detection signal resulting from non-linearity or non-ideality of the modulator. Alternatively or even additionally, it is possible to use the monitor channel for linearizing the modulator. In other words, the signal detected by the modulator monitor can be used for regulating the input voltage of the modulator (for instance a piezo or voice coil). This results in a basically linear behavior or a basically constant modulation frequency over the entire stroke.

FIG. 1 shows a Phase Analysis Light Scattering (PALS) apparatus 50 for measuring electromobility of particles in a sample according to an exemplary embodiment of the invention.

The PALS apparatus 50 comprises a light source 1 (such as a laser diode, particularly a single-mode laser diode) configured for generating coherent monochromatic light 2. The coherence length may be at least the difference of path lengths of beams interfering with one another (for instance may be at least 5 cm, particularly may be at least 20 cm). This coherent light 2 may be generated by a laser diode or the like. The light source 1 may emit optical light, i.e. light 2 in the visible range between 400 nm and 800 nm, or may emit light 2 in another suitable frequency range (such as infrared or ultraviolet). Coherent means in this context that the light 2 has a well-defined phase relation over a distance of at least the length of the beam path length difference of FIG. 1. The original light beam 2 emitted by the light source 1 is split by a beam splitter 3 into a part 14 and a remaining part 35.

Moreover, the PALS apparatus 50 comprises a reciprocating modulator 6 arranged for modulating a first part 5 of the light 2 generated by the light source 1. The modulator 6 serves for phase modulating the first part 5 of the generated light 2. In the shown embodiment, the modulator 6 is a piezo modulator, but it can also be a voice coil or any other kind of modulator. In practice, the modulator 6 may show deviations from an ideal, for instance linear, behavior, for example as a result of intrinsic artifacts of the piezo body, aging effects, and external influences such as environmental pressure or temperature.

Furthermore, a sample cell 16 may be provided in which a fluidic sample under analysis may be accommodated. An electric field may be applied to the sample, for instance by electrodes 17 indicated schematically in FIG. 1. The sample may be accommodated within the sample cell 16, and the electric field may be applied to the sample under analysis so as to generate a motion as a consequence of the generated electric force. The sample cell 16 receives, as shown in FIG. 1, the second part 14 of the light 2 generated by the light source 1.

A modulator monitor 13 is provided and configured as a single photodiode. The modulator monitor 13 monitors behavior of the modulator 6 by detecting a first part 33 of light 8 coming from the modulator 6.

Furthermore, the PALS apparatus 50 comprises a light detector 26 in the form of another single photo-detection element and being configured for detecting an interference between a second part 21 of light 8 coming from the modulator 6 and light 19 received from the sample cell 16, i.e. after interaction with the sample to which an electric field is applied.

Additionally, a retro-reflector 7 is formed by two angularly arranged reflection mirrors which are configured for applying a double reflection of the first part 5 of the generated light 2 on the modulator 6. Although not shown in FIG. 1, the modulator 6 is driven by a drive unit such as a voltage source for applying an electric voltage to the piezo body of the modulator 6.

The modulator monitor 13 is configured for detecting interference between the first part 33 of the light 8 coming from the modulator 6 and a non-modulated third part 11 of the generated light 2.

FIG. 1 furthermore shows that a determining unit 30 (such as a processor) is provided and configured for determining the electrophoretic mobility of the sample in the sample cell 16. This determining can be performed based on an electric signal measured by the light detector 26 upon propagation of detection light 24 onto the light detector 26. A signal measured by the modulator monitor 13 may be used as well for this determining. In other words, the signal detected by the light detector 26 can be corrected by using information about the non-ideal behavior of the modulator 6 as determined by the modulator monitor 13.

A reflector mirror 20 is arranged between the sample cell 16 and the light detector 26 and is configured for the directing only a part of the light having interacted with the sample in the electric field to the light detector 26, which part has been scattered into a predefined angular range. This angular range is defined by the geometry of the reflector mirror 20 relative to the light detector 26. Only light being reflected under an appropriate angle, so that it impinges on the light detector 26, contributes to the determining of the electromobility.

A beam splitter 4 is arranged for splitting a light beam coming from the light source 1 into the first part 5 of the generated light 2 and into third part 11 of the generated light 2. A beam combiner 10 is arranged for combining the first part 33 of the light 8 coming from the modulator 6 and the third part 11 of the generated light 2 and for directing a combined light beam 12 to the modulator monitor 13.

Moreover, a variable attenuator 22 is provided and arranged between the modulator 6 and the light detector 26 for adjusting an intensity of the second part 21 of the light 8 coming from the modulator 6 and reaching the light detector 26. In a similar way, another variable attenuator 15 is arranged between the light source 1 and the sample cell 16 for adjusting intensity of the second part 14 of the generated light 2 reaching the sample cell 16. Therefore, intensities of the light beams interfering downstream of a beam combiner 23 for forming detection light 24 may be adjusted to a desired value so as to obtain a meaningful result at the light detector 26.

Beam stops 34, 18, 25 are arranged at certain positions in the propagation paths.

In operation, the light source 1 is producing coherent primary light beam 2. A small fraction of this primary light beam 2 is split off by beam splitter 3. Another beam splitter 4 divides the beam which was split off into two beams or parts 5 and 11. The transmitted part 5 is retro-reflected by a pair of mirrors 7 which are mounted in an angle of 90°. This retro-reflector is phase-modulating the reflected beam or part 8 by modifying the optical path length for example by a the motion of a piezoelectric actuator or modulator 6. Another beam splitter 9 reflects a fraction or part 21 of the modulated beam and transmits the rest. The transmitted part of the modulated beam is overlaid with the unmodulated reference beam or part 11 by a further beam splitter acting as a beam combiner 10 in order to generate the monitor beam or part 12. The beat in the monitor beam or part 12 is detected by a photosensitive detector (such as a photodiode) constituting modulator monitor 13. The second unused output beam of beam splitter 10 is guided into beam trap or beam stop 34.

The sample beam or part 14 is the main part of the primary light beam 2 which is transmitted through beam splitter 3. The intensity of the sample beam is adjusted by variable attenuator 15. The sample is placed in sample cell 16 with immersed electrodes 17. The portion of the sample beam which is transmitted through the sample cell 16 is trapped by beam trap or beam stop 18. The scattered light at one selected scattering angle is reflected by mirror or reflector 20 and brought to interference by beam splitter 23 with the reference beam or part 21, which was adjusted in intensity by the attenuator 22. One output beam of beam splitter 23 is detected by photosensitive light detector 26 (such as a photodiode), while the other one is trapped by beam trap or beam stop 25.

Figure 2:
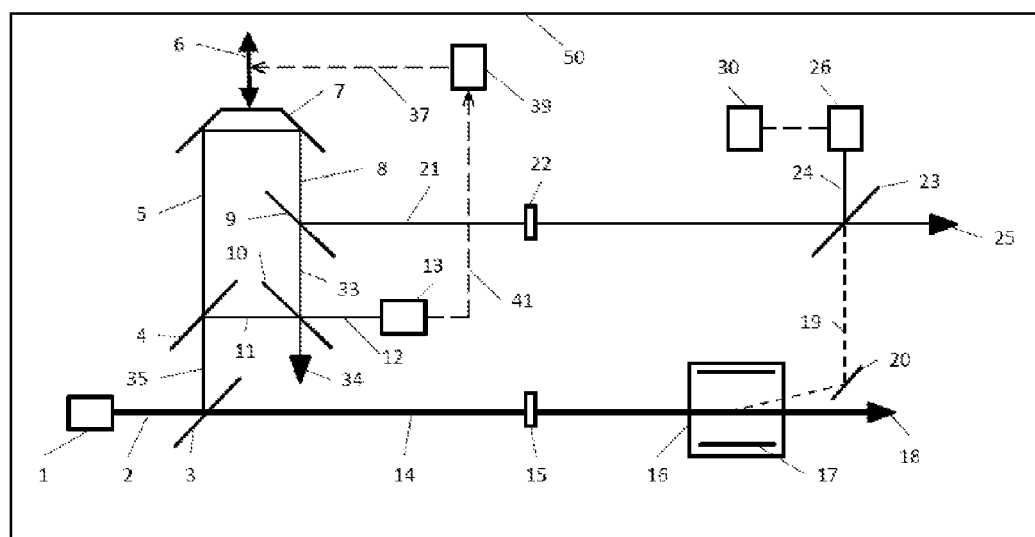
FIG. 2 illustrates a PALS apparatus according to another exemplary embodiment of the invention.

FIG. 2 shows a PALS apparatus 50 according to another exemplary embodiment of the invention.

The PALS apparatus 50 of FIG. 2 is very similar to the PALS apparatus 50 of FIG. 1 but has the following modifications: In the embodiment of FIG. 2, the modulator monitor 13 is configured for regulating a drive signal 37 applied by a drive unit 39 (such as a voltage or current source) to the piezo or voice-coil element of the modulator 6 for moving the modulator 6 based on the interference signal of light beams 33 and 12. The modulator monitor 13 provides the drive unit 39 with this interference signal, wherein the drive unit 39 then adapts the drive signal 37 for linearizing the motion of the modulator 6. Therefore, in contrast to the embodiment of FIG. 1, the PALS apparatus 50 of FIG. 2 does not correct the detection signal as detected by the light detector 26 to compensate for a non-linearity of the modulator 6, but in contrast to this provides a feedback signal via a feedback line 41 to the drive unit 39 of the modulator 6, thereby compensating for deviations from a desired behavior by an impact on the drive characteristic of driving the modulator 6.

The detection of the monitor beam or part 12 may be used to enhance and linearize the performance of the piezoelectric actuator/modulator 6. The signal measured with the photosensitive detector or modulator monitor 13 controls the input voltage of the modulator 6 in order to linearize the characteristic of the modulator 6 and hence stabilize the reference beam.

In the following, some alternative detection options will be described: The shown detection of the monitor signal by photosensitive detector or modulator monitor 13 and beam trap 34 is equivalent to another detection scheme where 13 and 34 are exchanged. Alternatively, both output beams of beam splitter or beam combiner 10 could also be used for balance detection of photosensitive detectors in 13 and 14.

The same alternative holds for the detection of the measurement signal. Light detector 26 and beam trap 25 can be exchanged. Both output beams of beam splitter or beam combiner 23 can be used for balance detection of detectors in 25 and 26.

FIG. 3 is a block diagram of a method 100 of measuring information which is indicative of electromobility in a sample accommodated in a sample cell to which an electric field is applied according to an embodiment of the invention.

The method 100 comprises accommodating a sample in a sample cell (see block 110), applying an electric field to the sample (see block 120) and generating coherent light (see block 130). Then, a first part of the generated light is modulated by an interaction with a modulator for instance a moving modulator (see block 140). A second part of the generated light is received in the sample cell for interaction with the sample in the electric field (see block 150). The modulator is monitored by detecting interference between a first part of the light coming from the modulator and an unmodulated third part of the generated light (see block 160). Separately from the monitoring, interference is detected between a second part of light coming from the modulator and light received from the sample cell, wherein the detected signal includes the information which is indicative of electromobility in the sample (see block 170).

It should be noted that the term "comprising" does not exclude other elements or steps and the "a" or "an" does not exclude a plurality. Also elements described in association with different embodiments may be combined.

Implementation of the invention is not limited to the preferred embodiments shown in the figures and described above. Instead, a multiplicity of variants are possible which use the solutions shown and the principle according to the invention even in the case of fundamentally different embodiments.

The invention claimed is:

1. An apparatus for measuring information which is indicative of electromobility in a sample, the apparatus comprising:
 a light source configured for generating coherent light;
 a modulator arranged for modulating a first part of the generated light;
 a sample cell for accommodating the measured sample, configured for applying an electric field to the sample, and arranged for receiving a second part of the generated light for interaction with the sample in the electric field;
 a modulator monitor configured for monitoring the modulator by detecting interference between a first part of the light coming from the modulator and an unmodulated third part of the generated light;
a light detector arranged separately from the modulator monitor and being configured for detecting interference between a second part of light coming from the modulator and light received from the sample cell, wherein the detected signal includes the information which is indicative of electromobility in the sample.

2. The apparatus of claim 1, wherein the modulator monitor is configured for continuously monitoring the modulator by detecting modulator information over a continuous time interval during at least a part of the entire duration of a Phase Analysis Light Scattering measurement.

3. The apparatus of claim 1, wherein the modulator monitor and the light detector are physically and spatially separate bodies.

4. The apparatus of claim 1, comprising a determining unit configured for determining the information indicative of electromobility of the sample based on the signal detected by the light detector and based on modulator information detected by the modulator monitor.

5. The apparatus of claim 4, wherein the determining unit is configured for determining the information by demodulating the signal detected by the light detector using the modulator information, particularly using directly the signal measured by the modulator monitor for demodulation.

6. The apparatus of claim 4, wherein the modulator information is indicative of a deviation of an actual modulator behavior from a target modulator behavior, particularly of at least one of the group consisting of a modulator artifact, a non-linear behavior of the modulator, an impact of environmental conditions such as temperature or pressure on the behavior of the modulator, and aging effects changing behavior of the modulator over time.

7. The apparatus of claim 4, wherein the determining unit is configured for manipulating the signal detected by the light detector using the modulator information to thereby at least partially compensate for a deviation between a target beat frequency and an actual beat frequency defined by the modulator.

8. The apparatus of claim 1, wherein the modulator monitor is configured for regulating a drive signal moving the modulator based on a signal detected by the modulator monitor resulting from the interference between the first part of the light coming from the modulator and the unmodulated third part of the generated light.

9. The apparatus of claim 8, wherein the modulator monitor is configured for regulating the drive signal to thereby linearize the behavior of the modulator.

10. The apparatus of claim 1, wherein the modulator monitor is configured as a single sensor element and/or the light detector is configured as a single sensor element.

11. The apparatus of claim 1, comprising:
a beam splitter arranged for splitting a light beam coming from the light source into the first part of the generated light and into a third part of the generated light;
a beam combiner arranged for combining the first part of the light coming from the modulator and the third part of the generated light and for directing the combined light to the modulator monitor.

12. The apparatus of claim 1, wherein a beam path from the light source via the modulator to the light detector and a beam path from the light source to the modulator monitor are apart from the sample cell and free of an interaction with the sample.

13. The apparatus of claim 1, wherein the modulator comprises a piezo body or voice coil to be moved by applying an electric drive signal configured to trigger the piezo to perform an elongation or motion in a range between 1 µm and 1000 µm, particularly in a range between 20 µm and 100 µm.

14. The apparatus of claim 1, comprising at least one of the following features:
the modulator is a movable, particularly a reciprocatible, optical path length modulator, or a modulator that modulates the refractive index which results in a modulation of the optical path length;
the modulator comprises a retro-reflector arrangement of two reflection mirrors configured for double-reflecting the first part of the generated light;
the modulator is configured for changing the optical path length for phase-modulating the first part of the generated light;
the apparatus comprises at least one optical element, particularly a reflector mirror, arranged in a beam path between the sample cell and the light detector and being configured for directing only a part of the light having interacted with the sample in the electric field towards the light detector which part has been scattering into a predefined angular range;
the apparatus comprises at least one optical element, particularly a reflector mirror, arranged in a beam path between the sample cell and the light detector and being configured for directing only a part of the light having interacted with the sample in the electric field towards the light detector which part has been scattering into a predefined angular range, wherein a center of the predefined angular range is slanted relative to a direction of the second part of the generated light impinging on the sample cell;
the apparatus comprises a reference beam intensity adjustment unit, particularly a variable attenuator, arranged in a beam path between the modulator and the light detector and being configured for adjusting intensity of the second part of light coming from the modulator;
the apparatus comprises a sample beam intensity adjustment unit, particularly a variable attenuator, arranged in a beam path between the light source and the sample cell and being configured for adjusting intensity of the second part of the generated light;
wherein the modulator monitor is configured for discontinuously monitoring the modulator by detecting modulator information only at a number of defined points of time spaced relative to one another over the duration of a Phase Analysis Light Scattering measurement;
wherein the modulator comprises a piezo drive configured for moving upon applying an electric drive signal to a piezoelectric body of the piezo drive;
wherein the modulation monitor is configured so that the unmodulated third part of the generated light propagates onto the modulation modulator without prior interaction with the sample in the sample cell;
wherein the apparatus is configured as a Phase Analysis Light Scattering apparatus for measuring electromobility by Phase Analysis Light Scattering;
wherein the apparatus is configured as a Laser Doppler Electrophoresis apparatus for measuring electromobility by Laser Doppler Electrophoresis.

15. A method of measuring information which is indicative of electromobility in a sample accommodated in a sample cell to which an electric field is applied, the method comprising:

generating coherent light;

modulating a first part of the generated light by an interaction with a, particularly moving, modulator;

receiving a second part of the generated light in the sample cell for interaction with the sample in the electric field;

monitoring the modulator by detecting interference between a first part of the light coming from the modulator and an unmodulated third part of the generated light;

separately from the monitoring, detecting interference between a second part of light coming from the modulator and light received from the sample cell, wherein the detected signal includes the information which is indicative of electromobility in the sample.

* * * * *